United States Patent [19]

Tung

[11] Patent Number: 5,427,768

[45] Date of Patent: Jun. 27, 1995

[54] CARBONATED SOLUTIONS FOR TREATING, MINERALIZING AND FLUORIDATING CALCIFIED TISSUES AND METHODS FOR THEIR USE

[75] Inventor: Ming S. Tung, Gaithersburg, Md.

[73] Assignee: American Dental Association Health Foundation, Gaithersburg, Md.

[21] Appl. No.: 81,476

[22] Filed: Jun. 23, 1993

[51] Int. Cl.[6] .................. A61K 7/16; A61K 7/18; A61K 9/12

[52] U.S. Cl. ........................ 424/52; 424/43; 424/44; 424/49; 424/602; 106/35; 433/215; 433/226; 433/228.1; 433/229

[58] Field of Search .............. 433/229, 228.1, 215, 433/226; 424/49, 52, 57; 106/35

[56] References Cited

U.S. PATENT DOCUMENTS

| | | | |
|---|---|---|---|
| Re. 33,161 | 2/1990 | Brown et al. | 433/199.1 |
| Re. 33,221 | 5/1990 | Brown et al. | 433/199.1 |
| 3,913,229 | 10/1975 | Driskell | 433/215 |
| 3,943,267 | 3/1976 | Randol | 424/49 |
| 4,048,300 | 9/1977 | Thomlinson et al. | 424/52 |
| 4,080,440 | 3/1978 | DiGuilio | 424/49 |
| 4,108,980 | 8/1978 | Duff | 424/52 |
| 4,140,760 | 2/1979 | Withington | 424/687 |
| 4,177,258 | 12/1979 | Gaffar et al. | 424/52 |
| 4,183,915 | 1/1980 | Gaffar | 424/52 |
| 4,283,385 | 8/1981 | Dhabhar et al. | 424/52 |
| 4,342,741 | 8/1982 | Aoki | 424/49 |
| 4,348,381 | 9/1982 | Gaffar | 424/52 |
| 4,397,837 | 8/1983 | Raaf et al. | 424/52 |
| 4,405,600 | 9/1983 | Besic | 424/57 |
| 4,515,770 | 5/1985 | Besic | 424/49 |
| 4,518,430 | 5/1985 | Brown et al. | 433/228.1 |
| 4,532,124 | 7/1985 | Pearse | 424/52 |
| 4,556,561 | 12/1985 | Brown et al. | 424/48 |
| 4,606,912 | 8/1986 | Rudy et al. | 424/52 |
| 4,610,873 | 9/1986 | Rudy et al. | 424/52 |
| 4,612,053 | 9/1986 | Brown et al. | 433/201.1 |
| 4,714,608 | 12/1987 | Rölla | 424/52 |
| 4,880,610 | 11/1989 | Constantz | 606/53 |
| 4,889,725 | 12/1989 | Veltman | 424/675 |
| 4,923,683 | 5/1990 | Sakuma et al. | 424/52 |
| 5,034,059 | 7/1991 | Constantz | 424/423 |
| 5,037,639 | 8/1991 | Tung | 424/57 |
| 5,047,031 | 9/1991 | Constantz | 606/77 |
| 5,053,212 | 10/1991 | Constantz et al. | 433/199.1 |
| 5,129,905 | 7/1992 | Constantz | 606/76 |
| 5,145,668 | 9/1992 | Chow et al. | 424/52 |
| 5,268,167 | 12/1993 | Tung | 424/52 |

OTHER PUBLICATIONS

Tung, et al., "Hydrolysis of Dicalcium Phosphate Dihydrate In The Presence Or Absence Of Calcium Fluoride" Basic Biological Sciences; Dent., J. Res. 64(1):2–5.

Patel, P R, et al. "Solubility of $CaHPO_4 \times 2H_2O$ In The Quaternary System $Ca(OH)_2$—$H_3PO_4$— $NaCl$—$H_2O$ at 25° C." J. Res. Nat. Bur. Stand.-78A:675–681 (1974).

Brown, W., et al. "Crystallography Of Tetracalcium (List continued on next page.)

Primary Examiner—Ronald W. Griffin
Attorney, Agent, or Firm—Allegretti & Witcoff, Ltd.

[57] ABSTRACT

This invention involves methods and compositions for preparation of unstable carbonated calcium phosphate solutions, which are supersaturated with respect to calcium phosphate solids and carbon dioxide and the use of such solutions for the treatment of dental tissue and hyposalivation. Specifically the methods include mixing a stable alkaline carbonated solution containing carbonate with a stable acidic calcium solution, either or both solutions also containing phosphate to create an unstable carbonated solution with respect to calcium phosphate and carbon dioxide. Also, the methods include adding aqueous solution to the solids containing calcium salts, phosphate salts and carbonate salts to create an unstable carbonated solution supersaturated with respect to calcium phosphate solids and carbon dioxide. The methods further include using alkaline solutions to remove the acidic residue from dental tissue and maintain cariostatic conditions.

8 Claims, No Drawings

OTHER PUBLICATIONS

Phosphate" J. Res. Nat. Bur. Stand. 69A 547–551 (1965).

Moreno, E. et al. "Stability of Dicalcium Phosphate Dihydrate in Aqueous Solutions and Solubility of Octocalcium Phosphate" Soil Science Society Proceedings 1960.

McDowell, et al. "Solubility of $CA_5(PO_4)_3 \times$ In The System $Ca(OH)_2$—$H_3PO_4$—$H_2O$ at 5°, 15°, 25° and 37° C." J. Res. Nat. Bur. Stand.–81A: 273–281 (1977).

Gregory, T. M. et al. "Solubility of B—$Ca_3(PO_4)_2$ in the System $Ca(OH)_2$—$H_3PO_4$ at 5°, 15°, 25° and 37° C." J. Res. Nat. Bur. Stand.—78A: 667–674 (1974).

Gregory, T. M., et al. "Solubility of $CaHPO_4 \times 2H_2O$ in the System $Ca(OH)_2$—$H_3PO_4$—$H_2O$ at 5°, 15°, 25°, and 37.5° C." J. Res. Nat. Bur. Stand. 74A:461–475 (1970).

Driskell, et al. "Development of Ceramic and Ceramic Composite Devices for Maxillofacial Applications" J. Biomed. Mater. Res. Symposium 6: 345–361 (1972).

Levine, R. S., et al. "Remineralisation of Natural Carious Lesions Of Enamel In Vitro" Brit. dent. J. 1974: 137, 132, Dental Caries Dental Enamel: Hydroxyapatite: 132–134.

Zimmerman, et al. "The Effect of Remineralization Fluids On Carious Lesions In Vitro" Brit. dent. J., 1974: 137, 132, Dental Caries Dental Enamel: Hydroxyapatite: 132–134.

Silverstone, et al. "Progressions of Caries–like Lesions In Vitro After Exposure To Synthetic Calcifying Fluids" IADR Abstract No. 283 (1979).

Wefel, J. S., et al. "Artificial Lesion Formation In $TiF_4$ and APF Treated Enamel" IADR Abstract No. 284 (1979).

Crall, J. J. et al. "Artificial Lesion Formation and Progression after Two–step Topical Fluorides" IADR Abstract No. 285 (1979).

Hiatt, W. H. et al. "Root Preparation I. Obturation of Dentinal Tubules In Treatment of Root Hypersensitivity" J. Periodontal: 373:380 (1972).

Gelhard, T. B. F. M., "Rehardening Of Artificial Enamel Lesions In Vitro" Caries Res. 13: 80–83 (1979).

Silverstone, "Remineralization Phenomena" Caries Res. II (Suppl. 1): 59–84 (1977).

Briner, W. W., "Significance Of Enamel Remineralization" 53 239–243 (1974).

NASA And Dentristry, "New–Tooth Enamel From Brushite Crystals" (Oct. 1977).

Pickel, F. D. "The Effects Of A Chewing Gum Containing Dicalcium Phosphate On Salivary Calcium And Phosphate" Ala. J. Med Sci. 2: 286–87 (1965).

Trautz, "Crystallographic Studies Of Calcium Carbonate Phosphate" Annals of the N.Y. Acad. Sci. 35, Article 1: 145–160 (1960).

Blumenthal, N. C. et al. "Effect Of Preparation Conditions On The Properties And Transformation Of Amorphous Calcium Phosphate" Mat. Res. Bull. 7: 1181–1190 (1972).

Posner, A. S., et al. "Synthetic Amorphous Calcium Phosphate And Its Relation To Bone Mineral Structure" Accts. Of Chem. Res. 8: 273–281 (1975).

Tung, M. S. et al. "An Intermediate State In Hydrolysis Of Amorphous Calcium Phosphate" Calcif Tissue Int 783–790 (1983).

LaGeros, R. Z. "Apatitic Calcium Phosphates: Possible Dental Restorative Materials" IADR Abstract No. 1482 J. Dent. Res. 61 (1982).

Tung M. S. et al. "The Effects of Calcium Phosphate Solutions on Permeability of Dentin:" J. Dent. Res. 65 Abstract No. 167 (1986).

Brown, et al. "Singular Points in the Chemistry of Teeth" IADR Abstract No. 120 J. Dent. Res. 54: 74 (1975).

Guide to Dental Materials and Devices, 7 Ed. p. 49 (ADA 1974).

Aboba Takaaki, et al., "Small–Angle X–Ray Scattering Study On The Transformation Of Amorphous Calcium Phosphate To Crystalline Apatite" Chem. Abstracts, vol. 91 No. 13, Abstract No. 105934g, (1979).

Ababa Takaaki, "X–Ray Diffraction Study On The Amorphous And Crystalline Components In Bone Mineral" Chem. Abstracts, vol. 91 No. 13, Abstract No. 105935r, (1979).

Termine, John D., et al. "Calcium Phosphate In Vitro" Chem. Abstracts, vol. 73, Abstract No. 12698–a, (1970).

Hong, Y. C. et al. (1989): "The Periapical Tissue Reactions to a Calcium Phosphate Cement in the Teeth of Monkeys," J. Dent. Res. (Submitted).

(List continued on next page.)

OTHER PUBLICATIONS

McDowell et al., "Solubility Study of Calcium Hydrogen Phosphate. Ion Pari Formation," Inorg. Chem. 10:1638–1643 (1971).

Tung, et al., "Effects of Calcium Phosphate Solutions on Dentin Permeability." vol 19 No. 8, J. of Endodontic (1983).

Brown, "Solubilities of Phosphates and Other Sparingly Soluble Compounds" from Griffith et al., Environmental Phosphorous Handbook (John Wiley & Sons, New York 1973).

De Rijk, et al. (1986): Clinical Evaluation of an Hydroxyapatite Precipitate for the Treatment of Dentinal Hypersensitivity, Biomedical Engineering V. Recent *Developments*, Proc of 5th Southern Biomedical Engineering Conference, Subrata Saha, Ed., New York: Pergamon Press, pp. 336–339.

Lu, et al., (1988): New Attachment Following the Use of a Novel Calcium Phosphate System, J. Dent Res. 67:352, Abst. No. 1913.

Schreiber, et al. (1988): Remineralization of Root Caries Lesion by a Calcium Phosphate Slurry, J. Dent. Res. 67: Abst. No. 255.

Sugawara et al, (1987): A Calcium Phosphate Root Canal Sealer-Filler J. Dent. Res. 66:296 Abst No. 1516.

Sugawara et al., (1988): Formation of Hydroxyapatite in Hydrogels from Tetracalcium Phosphate/Dicalcium Phosphate Mixtures, J. Dent. Res. (Submitted).

Matsuya, et al. "Effects of pH on the Reactions of Tetracalcium Phosphate and Dicalcium Phosphate," IADR Abstract 1991.

CARBONATED SOLUTIONS FOR TREATING, MINERALIZING AND FLUORIDATING CALCIFIED TISSUES AND METHODS FOR THEIR USE

This invention was made in the course of research, supported partially by the Government under grant DE 08916, awarded by the National Institute of Dental Research. The Government may have certain rights in the invention.

BACKGROUND OF THE INVENTION

1. Field of the Invention

This invention relates to certain carbonated calcium phosphate solutions that are unique in their applications as remineralizers of caries lesions, cavities and root erosions of the tooth, as mouth rinses and saliva substitutes. These solutions when further containing a fluoride compound can also be used for topical fluoridation of the teeth. When used for either fluoridation or mineralization these solutions prevent further tooth decay and actually restore the lesions caused by dental caries.

2. Description of the Prior Art

Dental lesions, cavities, exposed roots and dentin sensitivity all develop due to the loss of minerals from the dental tissue. In recent years, a large amount of research has been done in the field of mineralization and fluoridation to prevent and counteract such mineral loss. Tooth minerals are generally impure forms of hydroxyapatite, $Ca_5(PO_4)OH$. Therefore, the objectives of the research has been to deposit fluoride and apatite on and into the tooth, thus preventing further tooth decay, restoring the tooth and/or obturating the dentinal tubules.

U.S. Pat. No. 5,037,639 discloses the use of a carbonated solution for mineralizing and fluoridating calcified tissues. A continuation-in-part application Ser. No. (07/936,068) filed Aug. 26, 1992 further discloses the use of a carbonated calcium phosphate solution under pressurized carbonated solutions for mineralizing and fluoridating calcified tissues. The carbonated solution under pressurized carbon dioxide atmosphere offers a novel and useful method and composition to mineralize and fluoridate the tooth at the sites needed by controlling the pH and stability of the calcium phosphate fluoride solutions. However, the prior carbonated solutions needed to be maintained in a pressurized carbon dioxide atmosphere prior to application to sustain its beneficial effects. The present invention encompasses simple methods to prepare carbonated remineralizing solutions without the need to use a pressurized aerosol.

SUMMARY OF THE INVENTION

The potential for application of dental remineralization is vast. Dentists fill millions of cavities each year. If these cavities where remineralized rather than filled the general dental health of the public would be increased substantially, since remineralization results in a whole tooth. The present invention seeks to provide remineralization compositions and methods that can practically be applied under a dentist's care and virtually replace the need for filling of the teeth.

This invention involves methods and compositions for preparation of unstable carbonated calcium phosphate solutions, which are supersaturated with respect to calcium phosphate solids and carbon dioxide. The invention takes advantage of the fact that at alkaline pH aqueous solutions are capable of maintaining a greater amount of phosphate ions and carbonate ions in solution under atmospheric conditions. These alkaline solutions can then be mixed with acidic calcium solutions to create carbonated solutions useful for treating dental tissue.

When used to treat dental tissue the carbonated solutions of the present invention will deposit calcium phosphate compounds with or without fluoride on and in the tooth when applied for the prevention and/or repair of tooth weaknesses such as dental caries, exposed root, or dentin sensitivity. The deposition of the calcium phosphate compounds is controlled by the pH of the carbonated solutions. The pH of the solutions increases as carbon dioxide escapes and this facilitates the precipitation of the calcium phosphates over a range of time as needed.

In addition, it has been discovered that high pH and relatively high pH carbonated solutions are useful as mouth rinses for preventing cavities. Such mouth rinses create a basic oral environment, thus removing acid from the teeth and preventing the resulting cavities.

The advantages of the use of the calcium phosphate solution of the present invention as compared to the solutions and slurries of the prior art are many. Most importantly, the use of the compounds and methods of the invention allows for rapid formation of apatite upon dental tissues. Therefore, remineralization of the teeth can be achieved more quickly. In addition, the present invention provides for remineralization and fluoridation simultaneously when the carbonated solutions contain a fluorine compounds.

Another significant advantage is that the present invention will not damage the teeth due to a large change in pH during the remineralization process.

Yet another advantage of the present invention is the provision of a composition for remineralization of teeth which can be easily formulated and easily applied to the teeth.

Still another advantage of the present invention is the easy formulation of remineralizing carbonated solutions from solid powders.

And still a further advantage of the present invention is the provision of a composition which can be easily prepared and easily taken as an artificial saliva for individuals suffering from hyposalivation.

Thus, the present invention provides compositions and methods for remineralization of caries lesions that are practical for the use in a clinic environment. The invention also provides compositions and methods for the rapid fluoridation of teeth by the use of fluoride containing carbonated calcium phosphate solutions.

Further objects of the inventions will become apparent with the following description of the preferred embodiments and claims.

DETAILED DESCRIPTION OF THE PREFERRED EMBODIMENTS

The present invention provides the compositions and methods that can remineralize and/or fluoridate the tooth and, in the case of exposed root and dentin sensitivity, obstruct the dentinal tubules. The solution can be used as mouth rinse. When properly formulated, this carbonated calcium phosphate solution can be used as an artificial saliva to serve as a replacement modality for individuals exhibiting hyposalivation. The solutions may further contain other beneficial ions such as fluorides, hydrogen peroxide and strontium.

The inventor has found that under atmospheric conditions, in an aqueous solution the maximum concentration of carbonate ions in equilibrium with the carbon dioxide in the air increases dramatically with the increase in the pH of the solution. The data is shown in the Table 1 below.

TABLE 1

CONCENTRATION OF TOTAL CARBONATE IN THE 30 mM POTASSIUM DIHYDROGEN PHOSPHATE SOLUTION UNDER 0.00033 ATM $CO_2$ PRESSURE. THE pH WAS ADJUSTED BY ADDITION OF KOH.

| pH | TOTAL CARBONATE (mM) | KOH ADDED (mM) |
|---|---|---|
| 4.59 | 0.0116 | 0 |
| 6.62 | 0.0373 | 10 |
| 7.19 | 0.109 | 20 |
| 8.25 | 1.18 | 30 |
| 9.09 | 9.09 | 40 |
| 9.32 | 16.9 | 50 |
| 9.45 | 24.3 | 60 |
| 9.53 | 31.3 | 70 |
| 9.64 | 44.7 | 90 |
| 9.74 | 63.9 | 120 |
| 9.81 | 82.4 | 150 |
| 9.84 | 94.5 | 170 |
| 9.89 | 112 | 200 |

This property makes it possible to prepare stable alkaline carbonated solutions that contain a large quantity of carbonate ions. Therefore, by increasing the pH, a solution containing a high concentration of carbonate can be maintained without the need for maintaining the solution under a pressurized carbon dioxide atmosphere to keep the carbon dioxide from escaping the solution.

These stable alkaline carbonated solutions are useful unto themselves as mouth rinses. The solutions act as buffers to create an oral environment with a basic pH. This basic environment will remove acid from the dental surface and thereby prevent the formation of cavities.

In a particularly preferred embodiment, the alkaline carbonated solutions of the present invention contain phosphate. Such solutions are stable with respect to both carbonate and phosphate. These alkaline carbonated phosphate solutions can be mixed with stable aqueous solutions containing high concentration of calcium ions at acidic pH. The resulting mixed solutions are supersaturated with respect to calcium phosphate and carbon dioxide. These mixed calcium phosphate solutions thus contain high calcium and phosphate concentrations at lower pH (preferably 5 to 7.5). Because of the supersaturated nature of the mixed solutions, calcium phosphate compounds will precipitate out of the mixed solution as the pH of the solution increases due to the release of carbon dioxide to the air. Therefore, when the mixed solution is put in the mouth, carbon dioxide will be released and calcium phosphate will precipitate on and in the teeth. The calcium phosphate then reacts with the dental tissue and forms apatite.

The pH of the alkaline carbonated solutions is preferably between 8 and 12 and more preferably between 9 and 10. The desire pH and concentrations of the mixed carbonated calcium phosphate solution will determine what the acid concentration of the acidic calcium solution should be; the acid concentration is such as to make the pH of the mixed carbonated calcium phosphate solutions in the preferred range of 5 to 7.5.

The mixed solutions with the same compositions and properties as the above solutions can also be obtained by mixing a stable alkaline carbonated solution that contains a large quantity of carbonate under atmospheric conditions with a stable acidic calcium phosphate solution. In this system, the phosphate originates from the acidic solution, rather than the alkaline solution. The phosphate ions may also originate from both solutions, i.e., both the alkaline carbonated solution and the acidic calcium solution may include phosphate ions.

The mixed solution can also be obtained from the dissolution of solids in water. Stable solid powders containing all the ingredients in the mixed solutions can be created. These powders contain a mixture of calcium salts, phosphate salts, solid acid (such as acetic acid and/or citric acid) and carbonate salts with or without fluoride. When water is added to these powders, the solids will dissolve rapidly and the same carbonated calcium phosphate solutions as the mixed solutions can be obtained. These solutions can similarly be applied to dental surfaces for the prevention and repair of caries lesions, cavities, exposed roots and dentin sensitivity.

The final mixed carbonated solutions of the present invention may further include other beneficial components including: complex fluorides, such as monofluorophosphate, fluorosilicates and fluorostannates; antiseptic agents, such as chlorhexidine; and further mineralizing materials, such as strontium. When used as artificial saliva, the final mixed carbonated solution of the present invention may further contain mucins, carboxymethylcellulose (CMC), and a sweetner, such as sorbitol or xylitol. The final mixed solution may also include hydrogen peroxide as an antiseptic agent. However, hydrogen peroxide is particularly preferred when the final mixed carbonated solution is created by dissolving powder in water. While hydrogen peroxide can be included in the alkaline carbonated solution and acidic solution mixture, under some conditions, it may render those solutions unstable.

The following examples serve to illustrate the composition and method of invention, but are in no way limiting thereto.

EXAMPLE 1

A first carbonated solution contains 50.6 mM of $K_2CO_3$, 7.4 mM of $KH_2PO_4$ and 12.6 mM of $H_3PO_4$ with pH of 9.69 and a second solution contains 33 mM of $Ca(NO_3)_2$ and 50.6 mM of acetic acid with pH of 2.5. Both solutions are stable under atmospheric pressure. When the two solutions are mixed, the mixed solution has the pH of 6.4 and is supersaturated with respect to calcium phosphate and carbon dioxide under atmospheric pressure. As the carbon dioxide evaporates the pH of the solution increases and calcium phosphate precipitates out of solution.

EXAMPLE 2

The procedure of EXAMPLE 1 is repeated, except that phosphate compounds are added to the acidic calcium solution, instead of the alkaline solution. A first solution contains 50.6 mM $K_2CO_3$ with a pH of 11.24, and a second stable calcium phosphate solution contains 7.4 mM $KH_2PO_4$, 12.6 mM $H_3PO_4$, 33 mM $Ca(NO_3)_2$ and 50.6 mM acetic acid with a pH of 2.29. Both solutions are stable under atmospheric pressure. When the two solutions are mixed, the mixed solution has the pH of 6.4 and is supersaturated with respect to calcium phosphate and carbon dioxide under atmospheric pressure. As the carbon dioxide evaporates, the pH of the solution increases and calcium phosphate precipitates out of the solution.

EXAMPLE 3

A solid powder containing 54 mg calcium nitrate, 38 mg tripotassium phosphate, 3.5 mg potassium monohydrogen phosphate, 30.4 mg acetic acid and 50.7 mg potassium bicarbonate is created. 20 mL of water is added to the solid powder, the powders dissolve quickly and creates a solution having the same properties as the mixed solution in EXAMPLE 1, i.e. the solution has the pH of 6.4 and is supersaturated with respect to calcium phosphate and carbon dioxide under atmospheric pressure. As the carbon dioxide evaporates the pH of solution increases and calcium phosphate precipitates. Therefore, this solution can be applied directly to the tooth as a mineralizing solution.

EXAMPLE 4

A carbonated solution is prepared according to the procedure of EXAMPLE 1. The mixed solution is promptly applied directly to the dental tissue. Carbon dioxide escapes from the solution and calcium phosphate precipitates out of solution and is deposited on and into the dental tissue.

EXAMPLE 5

A carbonated solution is prepared according to the procedure of EXAMPLE 3. The solution is then promptly applied directly to the dental tissue. Carbon dioxide escapes from solution and calcium phosphate precipitates out of solution and is deposited on and into the dental tissue.

EXAMPLE 6

A carbonated solution is prepared according to the procedure of EXAMPLE 1, except that the acidic calcium solution also includes 1 mM fluorosilicate ions.

EXAMPLE 7

A carbonated solution is prepared according to the procedure of EXAMPLE 1, except that the acidic calcium solution also includes 1 mM fluorostannate ions.

EXAMPLE 8

A carbonated solution is prepared according to the procedure of EXAMPLE 1, except that the carbonated phosphate solution also contains 5 mM fluoride ions.

EXAMPLE 9

A carbonated solution is prepared according to the procedure of EXAMPLE 1, except that the acidic calcium solution also contains 33 mM strontium ions.

EXAMPLE 10

A carbonated solution is prepared according to the procedure of EXAMPLE 3, except that the solid mixture also includes 2.5 mM fluorine compound.

EXAMPLE 11

A carbonated solution is prepared according to the procedure of EXAMPLE 3, except that the solid mixture also includes 0.33 mM strontium compound.

EXAMPLE 12

A stable alkaline carbonated solution is created, containing 30 mM $K_2CO_3$ and 50 mM $K_2HPO_4$ at a pH of 10.6. This alkaline carbonated solution is used as a mouth rinse and removes acidic residue from the teeth thereby preventing cavities which might have resulted from the acidic residue.

The preferred embodiment of the present invention is now fully described. The above description, however, is only illustrative of the invention and is not intended to limit the invention in spirit or scope. Only the following claims and their equivalents limit the scope of the invention.

What I claim is:
1. A method of treating dental tissue comprising:
  (1) mixing a stable nonpressurized alkaline carbonated solution containing sufficient carbonate with a stable nonpressurized acidic solution containing calcium ions where either or both said solutions contain phosphate ions, to create a mixed solution supersaturated with calcium phosphate and carbon dioxide; and
  (2) promptly applying the mixed solution to the dental tissue whereby the carbon dioxide escapes and calcium phosphate is deposited on and in the dental tissue.
2. The method of claim 1 wherein either or both alkaline solutions further contain fluoride ions.
3. The method of claim 1 wherein the stable acidic solution further contains complex fluoride ions.
4. The method of claim 3 wherein the complex fluoride is fluorosilicate.
5. The method of claim 3 wherein the complex fluoride is fluorostannate.
6. The method of claim 1 wherein the pH of the stable alkaline solution is at least about 8.
7. The method of claim 1 wherein the stable acidic solution further contains strontium ions.
8. The method of claim 1 wherein either or both solutions further contain chlorhexidine compounds.

* * * * *